United States Patent [19]

Brusky

[11] Patent Number: 5,531,731
[45] Date of Patent: Jul. 2, 1996

[54] TAPE FASTENER FOR CONVEYING INFORMATION AND METHOD OF MANUFACTURE

[75] Inventor: Carl J. Brusky, Appleton, Wis.

[73] Assignee: Kimberly-Clark Corporation, Neenah, Wis.

[21] Appl. No.: 301,935

[22] Filed: Sep. 7, 1994

[51] Int. Cl.⁶ .................................................. A61F 13/15
[52] U.S. Cl. .............................. 604/390; 604/386; 2/244; 2/111; 428/42.1
[58] Field of Search ................................ 604/358, 385.1, 604/386–390, 393, 396; 602/55, 57; 450/81; 2/244, 111, 112; 428/40

[56] References Cited

U.S. PATENT DOCUMENTS

| | | | |
|---|---|---|---|
| 4,082,873 | 4/1978 | Williams | 428/40 |
| 4,182,789 | 1/1980 | Castelluzzo | 428/40 |
| 4,249,532 | 2/1981 | Polansky et al. | 604/385.1 X |
| 4,424,244 | 1/1984 | Puskadi | 428/40 |
| 4,500,316 | 2/1985 | Damico | 604/389 |
| 4,578,298 | 3/1986 | Nagafuchi | 428/40 |
| 4,662,875 | 5/1987 | Hirotsu et al. | 604/389 |
| 4,699,823 | 10/1987 | Kellenberger et al. | 428/219 |
| 4,753,649 | 6/1988 | Pazdernik | 604/389 |
| 4,778,701 | 10/1988 | Pape et al. | 428/40 |
| 4,798,603 | 1/1989 | Meyer et al. | 604/378 |
| 4,825,763 | 5/1989 | Truskolaski et al. | 101/488 |
| 5,096,424 | 3/1992 | Carlberg | 434/262 |
| 5,133,707 | 7/1992 | Rogers et al. | 604/389 |
| 5,147,343 | 9/1992 | Kellenberger | 604/368 |
| 5,168,002 | 12/1992 | Maietti | 428/352 |
| 5,225,260 | 7/1993 | McNaul et al. | 428/40 |
| 5,275,588 | 1/1994 | Matsumoto et al. | 604/372 |
| 5,288,546 | 2/1994 | Roessler et al. | 428/284 |
| 5,294,470 | 3/1994 | Ewan | 428/40 |
| B1 4,315,508 | 11/1988 | Bolick | 604/392 |

*Primary Examiner*—David H. Willse
*Assistant Examiner*—Mark O. Polutta
*Attorney, Agent, or Firm*—Thomas M. Gage; Thomas J. Mielke

[57] ABSTRACT

An absorbent article includes a garment with a tape fastener that provides for the display of printed information only when the garment is not being worn. The garment has opposite inner and outer surfaces and first and second waistband sections. The tape fastener, which is bonded to the first waistband section, includes an interior tape member and an exterior tape member. The interior tape member is bonded to the inner surface, and in one embodiment, contains the printed information. The exterior tape member includes a factory-bond section, which is bonded to the first waistband section, and a user-bond section, which is formed of a transparent material and includes an adhesive surface adapted to releasably engage the interior tape member. The printed information will not show through clothing when the garment is being worn.

10 Claims, 3 Drawing Sheets

TAPE FASTENER FOR CONVEYING INFORMATION AND METHOD OF MANUFACTURE

BACKGROUND OF THE INVENTION

The present invention is directed to a tape fastener for a garment. More particularly, the invention pertains to a garment with an adhesive tape fastener that conveys information except when the garment is being worn, at which time the information is hidden from view.

Tape fasteners have been used on a wide variety of garments, particularly disposable garments such as diapers and incontinence products. Such tape fasteners have included a tape member that extends between first and second waistband sections of a garment, thereby securing the garment about the wearer. In some instances, tape members have included printed information which is visible while the garment is worn. Such printed information may include the name of the garment manufacturer or a cartoon character.

While a garment with printed information visible during use may be acceptable for a garment worn by a child, it may not be appropriate for a garment worn by an adult. In particular, printed information which is visible during use may show through clothing. This can be displeasing and even embarrassing. Nevertheless, it is still desirable for tape fasteners to carry printed information which may be useful to the adult wearer.

Therefore, what is lacking and needed in the art is an improved tape fastener that provides for the display of printed information only when the garment is not being worn.

SUMMARY OF THE INVENTION

In response to the failure of the prior art to recognize the above-referenced problem or suggest a solution thereto, a new article has been developed. The article includes a garment with a tape fastener that conveys information when the garment is not being worn and while the garment is being applied. While the garment is being worn, however, the information is hidden from view.

In one aspect, the invention pertains to an article including a garment and a tape fastener. The garment has an inner surface, an opposite outer surface, first and second waistband sections, and an intermediate section which interconnects the waistband sections. The tape fastener is bonded to the first waistband section and includes an interior tape member and an exterior tape member. The interior tape member contains printed information and is bonded to the inner surface. The exterior tape member has a factory-bond section bonded to the first waistband section and a user-bond section. The user-bond section is formed of a transparent material and includes an adhesive surface adapted to releasably engage the interior tape member. The printed information is visible through the user-bond section when the user-bond section is releasably engaged with the interior tape member. This aspect of the invention allows the printed information to be visible when the tape fastener is a storage position and not be visible when the garment is worn.

In another aspect, the invention pertains to an article including a garment, a substrative member and a tape fastener. The substrative member contains printed information and is bonded to the garment on an inner surface of a first waistband section adjacent a longitudinal side. The tape fastener is bonded to the first waistband section and includes an interior tape member and an exterior tape member. The interior tape member is bonded to the inner surface to sandwich the substrative member between the interior tape member and the inner surface. The interior tape member is formed of a transparent material whereby the printed information is visible through the interior tape member. The exterior tape member has a factory-bond section bonded to the first waistband section and a user-bond section with an adhesive surface adapted to releasably engage the interior tape member. The user-bond section is formed of a transparent material whereby the printed information is visible through the interior tape member and the user-bond section when the user-bond section is releasably engaged with the interior tape member.

Yet another aspect of the invention relates to a method of making an article. The method includes the steps of: providing a garment having an inner surface, an opposite outer surface, first and second waistband sections, and an intermediate section which interconnects the waistband sections; providing a tape fastener comprising an interior tape member and an exterior tape member, the interior tape member containing printed information and having an adhesive surface and an opposite release surface, the exterior tape member having a factory-bond section and a user-bond section, the user-bond section formed of a transparent material and adapted to releasably engage the interior tape member; bonding the adhesive surface of the interior tape member to the inner surface; bonding the factory-bond section to the first waistband section such that the user-bond section is positioned to engage the release surface of the interior tape member; and releasably engaging the user-bond section and the interior tape member, the printed information being visible through the user-bond section.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
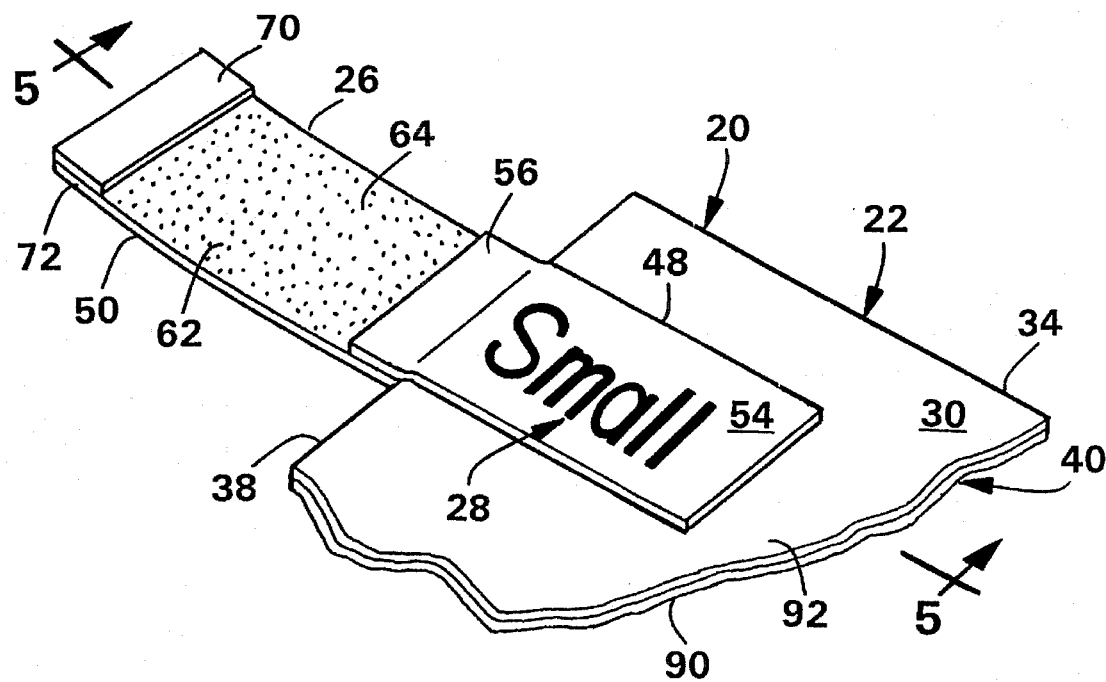
FIG. 1 is a perspective view of a tape fastener according to the present invention, shown bonded to a portion of an absorbent garment and in a ready position.

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed," disposed on" "disposed with, " "disposed at," "disposed near," and variations thereof are intended to mean that one element can be integral with another element, or that one element can be a separate structure bonded to or placed with or placed near another element.

(d) "elastic," "elasticized" and "elasticity" mean that property of a material by virtue of which it tends to recover its original size and shape after removal of a force causing a deformation.

(e) "liquid impermeable" when used to describe a layer or laminate means that urine will not pass through the layer or laminate under ordinary use conditions in a direction generally perpendicular to the plane of the layer or laminate at the point of liquid contact.

(f) "member" when used in the singular can have the dual meaning of a single element or a plurality of elements.

(g) "releasably attached," "releasably bonded," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

These terms may be defined with additional language in the remaining portion of the specification.

DETAILED DESCRIPTION OF THE PREFERRED EMBODIMENTS

With reference to FIGS. 1–4, an article 20 according to the present invention includes a garment 22 that is secured about the body of a wearer 24 with a plurality of tape fasteners 26. The tape fasteners 26 include printed information 28, in this case an indication of the size of the garment 22. The information 28 could also include directions for use of the garment 22, an indication of the source of the garment, decorative symbols, or the like. In one beneficial aspect of the invention, the information 28 is not visible when the garment 22 worn.

Figure 2:
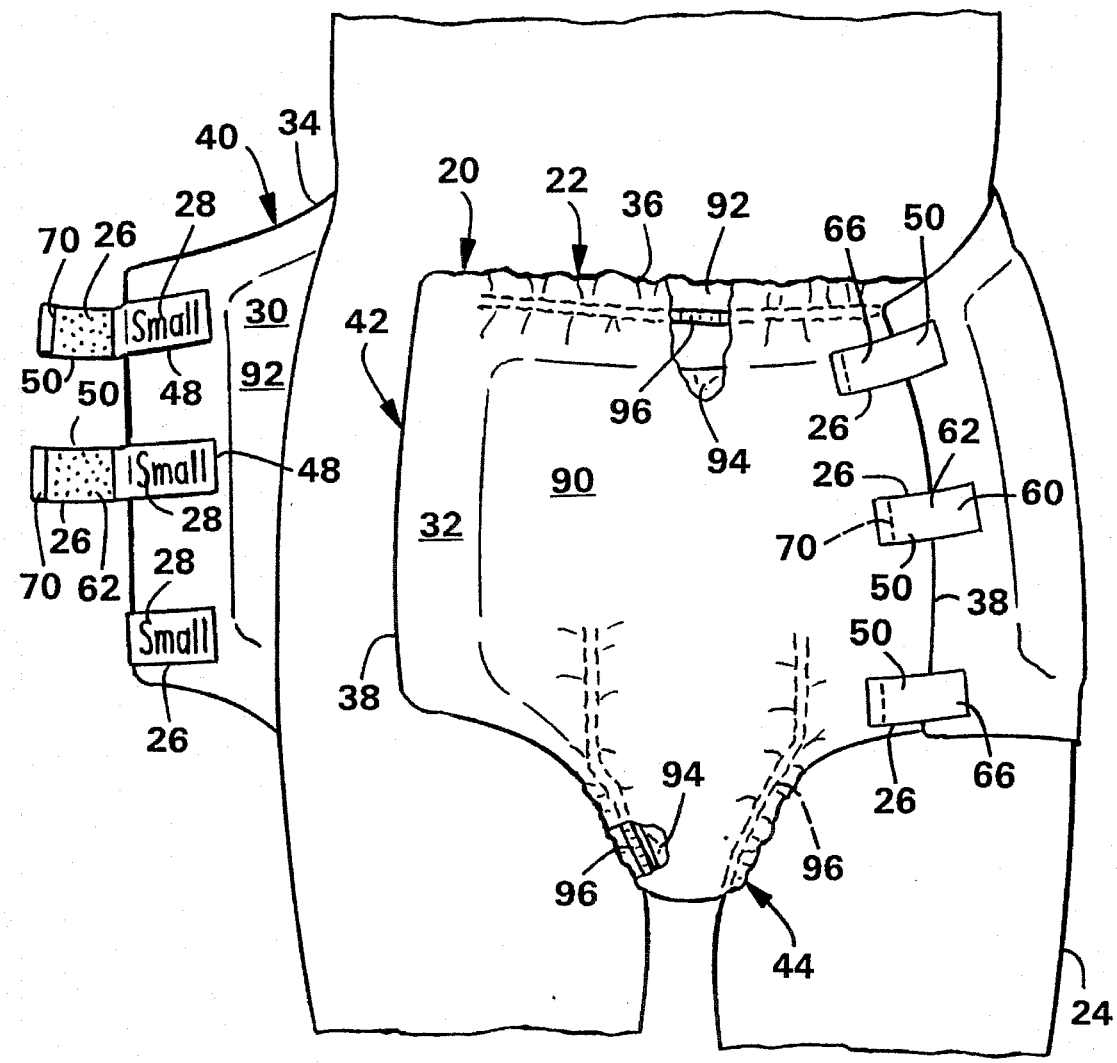
FIG. 2 is a front view of the garment partially shown in FIG. 1, positioned about a wearer while tape fasteners are being secured and with portions of the garment broken away for purposes of illustration.

The garment 22 is shown for purposes of illustration as a disposable, adult incontinence product. Other types of garments, for example diapers, health care garments, or the like, can also be used. The garment 22 has opposite major surfaces designated inner surface 30 and outer surface 32 (FIG. 2). The garment 22 includes a first end 34, an opposite second end 36, and longitudinal sides 38 extending between the first and second ends.

The garment 22 defines a first waistband section 40 contiguous with the first end 34 and extending inwardly therefrom, and an opposite second waistband section 42 contiguous with the second end 36 and extending inwardly therefrom. An intermediate section 44 is located between and interconnects the first and second waistband sections 40 and 42. When the garment 22 is placed about a wearer as illustrated in FIG. 2, the intermediate section 44 is generally the portion of the garment located in the crotch region of the wearer.

Figure 3:
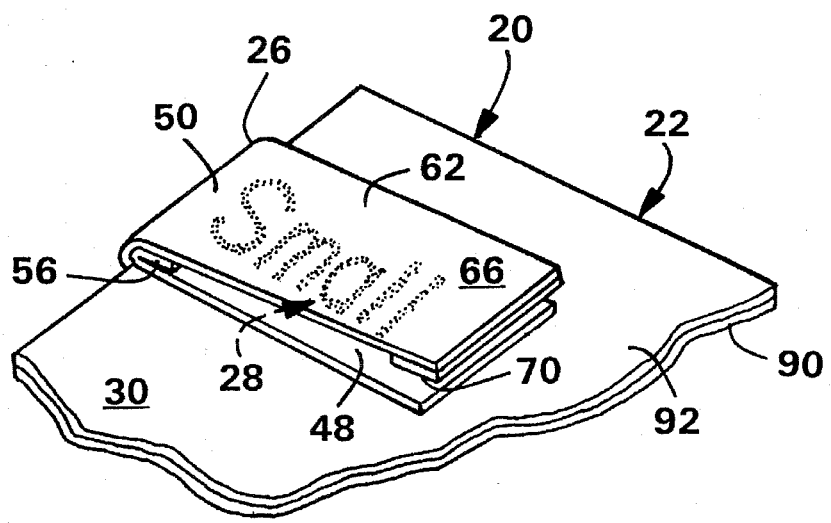
FIG. 3 is a perspective view similar to FIG. 1, but showing the tape fastener in a transition position.
Figure 4:
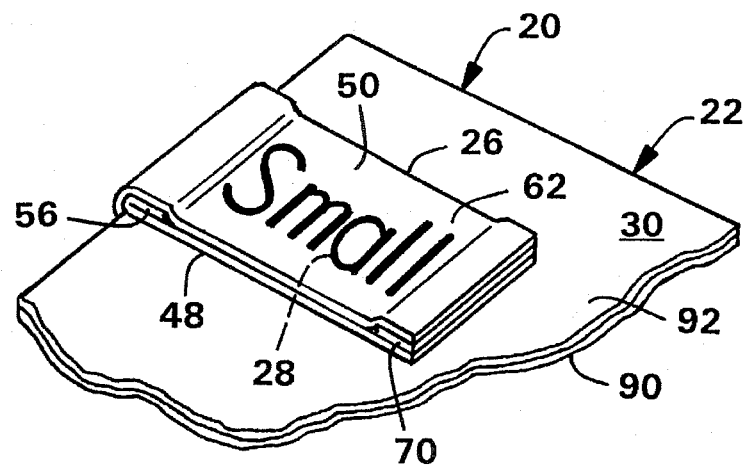
FIG. 4 is a perspective view similar to FIG. 1, but showing the tape fastener in a storage position.
Figure 5:
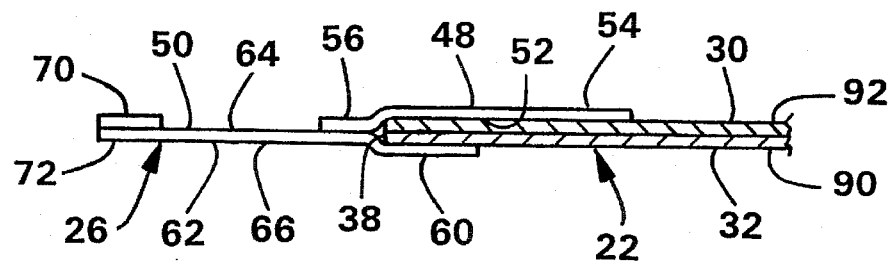
FIG. 5 is a section view taken generally from the plane of the line 5—5 in FIG. 1.

A representative tape fastener 26 is shown in different positions in FIGS. 1, 3 and 4. The positions will be referred to as a ready position (FIG. 1), a transition position (FIG. 3), and a storage position (FIG. 4). A section view of a tape fastener 26 in the ready position is shown in FIG. 5. Desirably, there is at least one opposing pair of tape fasteners 26 attached to the first waistband section 40. In the context of a disposable, adult incontinence product, there are more desirably three opposing pairs of tape fasteners 26 attached to the first waistband section 40 as illustrated in FIG. 2. In alternative embodiments, the location of the tape fasteners 26 can vary, such as at either or both of the sides 38 of either or both of the waistband sections 40 and 42.

Each tape fastener 26 includes an interior tape member 48 and an exterior tape member 50. The interior tape member 48 has opposite major surfaces designated adhesive surface 52 and release surface 54 (FIG. 5). An end portion of the interior tape member 48, referred to as an interface region 56, is directly bonded on the adhesive surface side 52 to the exterior tape member 50. The remaining portions of the interior tape member 48 are directly bonded on the adhesive surface side 52 to the inner surface 30 of the garment 22. More specifically, the adhesive surface 52 of each interior tape member 48 is bonded to the inner surface 30 of the first waistband section 40 proximate a longitudinal side 38 so that the interface region 56 is disposed adjacent the longitudinal side.

As best shown in FIG. 1, the interior tape member 48 contains the printed information 28 (not shown in FIG. 5). The printed information 28 may comprise letters, numbers, designs, logos, bar codes, other forms of human identifiable information, or combinations thereof. Printed information 28 thus includes any variable pattern or arrangement of colors, but would exclude for instance a solid color pattern or one not possessing variations detectable by the wearer of the garment 22. Printed information 28 in the form of alphanumeric information, consisting of alphabetic and numerical symbols, punctuation marks and mathematical symbols, is particularly useful to the wearer. The printed information 28 may be formed with ink, or the like. Suitable inks are available from a variety of vendors, such as Sun Chemical Corporation of Menasha, Wis.

The location of the printed information 28 may or may not be important, but the printed information 28 should be visible to the wearer from the release surface side 54 of the interior tape member 48. The information 28 may be printed on the adhesive surface side 52 or the release surface side 54. Alternatively, the information 28 may be formed within the substrate web forming the interior tape member 48 or within any adhesive or release coating used thereon (not shown). Suitable substrate webs for use in forming the interior tape member 48 comprise paper, polyolefin films, nonwovens, or the like. Suitable techniques for printing the information on the substrate web include flexographic, letterpress, or gravure printing techniques, or the like.

The adhesive surface 52 desirably has a suitable adhesive substance disposed thereon to bond the interior tape member 48 to the inner surface 30. Suitable adhesive substances include pressure sensitive adhesives available from 3M Company of Minneapolis, Minn., or Avery International, a business having a Specialty Tape Division with offices in Plainesville, Ohio. The adhesive substances desirably bond the interior tape member 48 to the inner surface 30 with greater strength than that which releasably bonds the exterior tape member 50 to the release surface 54.

The release surface 54 desirably has a suitable release coating disposed thereon (not shown). The release coating may comprise, for example, cured (cross-linked) poly dimethyl siloxane (PDMS). Release coating coated tapes are commercially available from vendors such as 3M Company and Avery International.

In one particular aspect of the invention, the interior tape member 48 comprises a polypropylene substrate web which has alphanumeric symbols printed thereon using a rotogravure printing technique. The information is covered with a release coating comprising polydimethylsiloxane to form the release surface 54. The opposite surface of the substrate web has a pressure sensitive adhesive formulation applied thereto to form the adhesive surface 52.

With particular regard to FIGS. 1, 2 and 5, the exterior tape member 50 includes a factory-bond section 60 and a user-bond section 62. The exterior tape member 50 also has opposite major surfaces designated adhesive surface 64 and exposed surface 66. The factory-bond section 60 is bonded to the first waistband section 40 while the user-bond section 62 is movable between the ready position of FIG. 1 and the storage position of FIG. 4. The adhesive surface 64 of the user-bond section 62 can be fastened, preferably releasably attached, to the second waistband section 42 of the garment 22 to secure the garment about the wearer.

In the illustrated embodiment, the factory-bond section 60 is bonded on the adhesive surface side 64 to the outer surface 32 of the garment 22. The factory-bond section 60 is bonded proximate a longitudinal side 38 so that user-bond section 62 is positionable against the interior tape member 48. The interface region 56 of the interior tape member 48 is desirably bonded to the adhesive surface 64 of the exterior tape member 50 at an intermediate section of the exterior tape member. Alternatively, of course, the factory-bond section 60 could be bonded to the inner surface 30 of the garment 22, such as between the inner surface and the interior tape member 48.

At least the user-bond section 62 and desirably the entire exterior tape member 50 is formed of a transparent material which allows the wearer to view the printed information 28 when the user-bond section is in the storage position (FIG. 4). The exterior tape member 50 desirably comprises a substrate member with a suitable adhesive substance disposed on one surface to form the adhesive surface 64. Both the substrate member and the adhesive substance should allow viewing therethrough. Suitable substrate members include polymer film materials, such as polypropylene, or polyethylene, or the like, and are available from various manufacturers, such as 3M Company. Suitable adhesive substances include pressure sensitive adhesives available from 3M Company. The adhesive substance allows the adhesive surface 64 to releasably engage the release surface 54 of the interior tape member 48.

Figure 6:
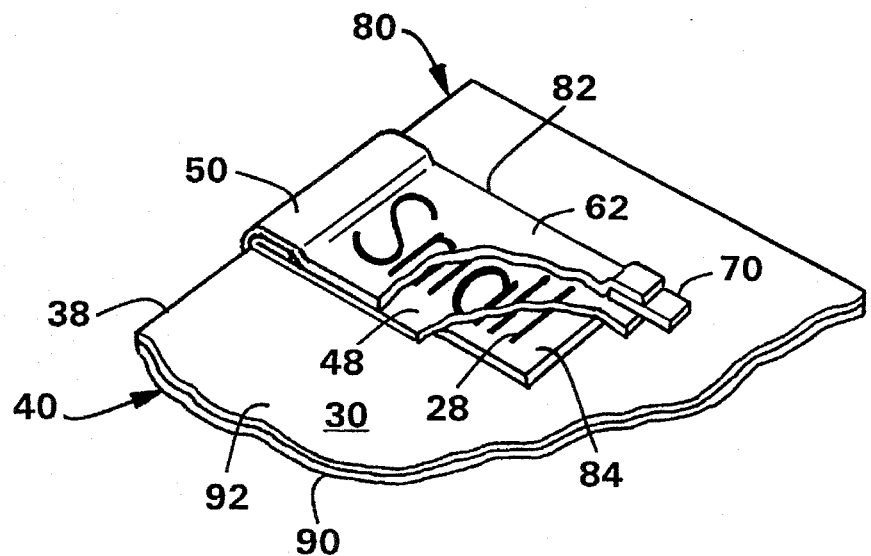
FIG. 6 is a perspective view similar to FIG. 4, but showing an alternative tape fastener according to the present invention, with portions broken away for purposes of illustration.

Each tape fastener 26 desirably but not necessarily also includes a finger tab 70. The finger tab 70 desirably comprises a layer of nonwoven material, such as an absorbent nonwoven fabric, bonded to the user-bond section 62 of the exterior tape member 50 at a terminal end region 72 thereof (FIGS. 1 and 5). The finger tab 70 can be coextensive with the terminal end region 72 or extend beyond the exterior tape member 50 (FIG. 6). Suitable finger tab 70 constructions are disclosed in U.S. Pat. No. 5,288,546 issued Feb. 22, 1994, to Roessler et al., which is incorporated herein by reference.

In FIG. 2, the garment 22 is illustrated positioned about a wearer 24 while the tape fasteners 26 are being secured. One of the tape fasteners 26, in particular the one on the right side of the wearer (left side of FIG. 2) and closest to the intermediate section 44, is still in the storage position. The other two tape fasteners 26 on that side are ready to be positioned and secured to the second waistband section 42. The three tape fasteners 26 on the left side of the wearer have already been secured to the outer surface 32 of the second waistband section 42. As clearly shown in FIG. 2, the printed information 28 is visible when the tape fasteners 26 are in either the storage position or the ready position, but not visible when the tape fasteners are secured to the second waistband section 42. Consequently, there is little likelihood that the printed information 28 will show through clothing. Because the printed information 28 is carried on or by the interior tape member 48 and the interior tape member faces the wearer when the product is worn, the printed information is not visible during use. Additionally, the transparent exterior tape members 50 allow better sight of the finger tabs 70, which can as a result be formed coextensive with the terminal end region 72 of the exterior tape members.

As illustrated by comparison of FIGS. 3 and 4, the printed information 28 need not be clearly visible when the tape fastener 26 is in the transition position (FIG. 3), that is when the user-bond section 62 is positioned near but not in contact with the interior tape member 48. The transparency of the exterior tape member 50, though, should be such that the printed information 28 is clearly visible to the wearer when the tape fastener 26 is in the storage position (FIG. 4).

An alternative absorbent article 80 is illustrated in FIG. 6, where components similar to those previously described have been given the same reference numeral. The article 80 includes a tape fastener 82 bonded to a first waistband section 40 of a garment 22. The article 80 also includes a substrative member 84 bonded to the inner surface 30 of the garment 22 adjacent one of the longitudinal sides 38. The substrative member 84 contains printed information 28.

The tape fastener 82 of the article 80 includes an interior tape member 48 and an exterior tape member 50, both of which are desirably formed of transparent material. The transparent interior tape member 48 is bonded to the inner surface 30, either directly or indirectly, to sandwich the substrative member 84 between the interior tape member and the inner surface, so that the printed information 28 is visible through the interior tape member. The exterior tape member 50 has a factory-bond section 60 (see FIGS. 4 and 5) bonded to the first waistband section 40 and a user-bond section 62 with an adhesive surface 64 (see FIGS. 1 and 5) adapted to releasably engage the interior tape member 48.

When the user-bond section 62 is releasably engaged with the interior tape member 48, the printed information 28 is visible through the interior tape member and the user-bond section 62. Desirably, however, when the user-bond section 62 is secured to the second waist section 42 during use, the printed information 28 is hidden from view due to the substrative member 84 and the printed information being positioned between the garment 22 and the wearer 24. The substrate member 84 may comprise a separate element formed of papers, polymer films, or the like, bonded to the inner surface, as illustrated. Alternatively, the substrate member 84 may comprise a printed portion of the inner surface 30 of the garment 22 (not shown).

Again with reference to FIG. 2, the absorbent garment 22 includes a substantially liquid impermeable outer cover 90, a substantially liquid permeable bodyside liner 92, and an absorbent assembly 94 sandwiched between the outer cover and the liner. The outer cover 90 and bodyside liner 92 are preferably longer and wider than the absorbent assembly 94, so that the peripheries of the outer cover and liner form margins which may be sealed together using ultrasonic bonds, thermal bonds, adhesives, or other suitable means. The absorbent assembly 94 may be attached to the outer cover 90 and/or the bodyside liner 92 using ultrasonic bonds, adhesives, or other suitable means. The garment 22 may also include additional components to assist in the acquisition, distribution and storage of waste material. For example, the garment 22 may include a transport layer, such as described in U.S. Pat. No. 4,798,603 issued Jan. 17, 1989, to Meyer et al., which is incorporated herein by reference.

In the illustrated embodiment, the garment 22 is hourglass-shaped with a length in the range of from about 40 to about 110 centimeters, and a width in the range of from about 15 to about 90 centimeters. Of course, the garment 22 may optionally be rectangular, T-shaped, I-shaped, or irregularly-shaped.

The garment 22 may optionally include elastic strands or ribbons 96 longitudinally orientated along each side 38 of the garment and/or along each end 34 and 36 of the garment and attached in a stretched condition to the outer cover 90, the liner 92, or both. The side elastic strands 96 are located in the intermediate section 44 and extend toward or into the first and second waistband sections 40 and 42. The elastic strands 96 along the ends 34 and 36 may be attached as described in U.S. Pat. No. 4,500,316 issued Feb. 19, 1985, to Damico, which is incorporated herein by reference. The elastic strands 96 may assist in holding the garment 22 against the body of the wearer and/or forming seals or gaskets with the body. Suitable elastic materials include a dry-spun coalesced multifilament elastomeric thread sold under the tradename LYCRA and available from I. E. Du Pont de Nemours and Company, a thin ribbon of natural or synthetic rubber, a hot melt elastomeric adhesive, or the like.

The outer cover 90 desirably comprises a material that is formed or treated to be liquid impermeable. Alternatively, the outer cover 90 may comprise a liquid permeable material and other suitable means, such as a liquid impermeable layer associated with the absorbent assembly 94, can be provided to impede liquid movement away from the absorbent assembly (not shown). The outer cover 90 may comprise a single layer of material or a laminate of two or more separate layers of material. The outer cover 90 may also be gas permeable, such that gases encountered during use of the absorbent garment are able to pass through the material under ordinary use conditions, over either all or part of its surface area. Suitable outer cover materials include films, wovens, nonwovens, laminates of films, wovens, and/or nonwovens, or the like. In one particular embodiment, the outer cover 90 comprises a liquid impermeable, polyethylene film.

In particular embodiments, the outer cover 90 might also include a landing zone patch (not shown) on the outer surface 32 in the second waistband section 42. The landing zone patch provides a target attachment zone for receiving the user-bond section 62 of the exterior tape members 50. One suitable landing zone patch is described in U.S. Pat. No. 4,753,649 issued Jun. 28, 1988, to Pazdernik, which is incorporated herein by reference.

The absorbent assembly 94 comprises materials adapted to absorb and retain liquid waste. The absorbent assembly 94 may be hourglass-shaped as illustrated, or rectangular, T-shaped, I-shaped or irregularly-shaped, and is narrower and desirably also shorter than the outer cover 90.

The absorbent assembly 94 may comprise various absorbent materials, such as an air-formed batt of cellulosic fibers (i.e., wood pulp fluff) or a coform material composed of a mixture of cellulosic fibers and synthetic polymer fibers. The absorbent assembly 94 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. and U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 94 may also include tissue layers or acquisition or distribution layers to help maintain the integrity of fibrous absorbents or transport liquids (not shown).

The bodyside liner 92 is formed of a liquid permeable material to allow liquid waste, and possibly semi-solid waste as well, to pass through the liner and be absorbed by the absorbent assembly 94. The liner 92 may comprise, for example, a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the liner may be treated with a surfactant to aid in liquid transfer.

The foregoing detailed description has been for the purpose of illustration. Thus, a number of modifications and changes may be made without departing from the spirit and scope of the present invention. For instance, alternative or optional features described as part of one embodiment can be used to yield another embodiment. Therefore, the invention should not be limited by the specific embodiments described, but only by the claims.

I claim:

1. An article, comprising:
    a garment having an inner surface intended to face the body during use, an opposite outer surface intended to face away from the body during use, first and second waistband sections, and an intermediate section which interconnects the waistband sections; and
    a tape fastener bonded to the first waistband section, the tape fastener comprising:
        an interior tape member containing printed information and bonded to the inner surface; and
        an exterior tape member having a factory-bond section bonded to the first waistband section and a user-bond section comprising an adhesive surface adapted to releasably engage the interior tape member, the user-bond section formed of a transparent material and the printed information being visible through the user-bond section when the user-bond section is releasably engaged with the interior tape member.

2. The article of claim 1, wherein the exterior tape member and the interior tape member are bonded together.

3. The article of claim 1, further comprising a finger tab bonded to a terminal end region of the user-bond section.

4. The article of claim 1, wherein the printed information is alphanumeric.

5. An article, comprising:
    a garment having an inner surface intended to face the body during use, an opposite outer surface intended to face away from the body during use, a first end, a first waistband section contiguous with the first end, a second end, a second waistband section contiguous with the second end, an intermediate section which interconnects the waistband sections, and longitudinal sides extending between the first and second ends; and a pair of tape fasteners bonded to the first waistband section, each of the tape fasteners positioned adjacent one of the longitudinal sides and comprising:

an interior tape member having a release surface containing printed information, an opposite adhesive surface bonded to the inner surface adjacent one of the longitudinal sides, and an interface region disposed adjacent the one longitudinal side; and an exterior tape member having a factory-bond section bonded to the outer surface in the first waistband section and a user-bond section adapted to releasably engage the interior tape member, the exterior tape member bonded to the interface region of the interior tape member, the user-bond section formed of a transparent material and the printed information being visible through the user-bond section when the user-bond section is releasably engaged with the interior tape member.

6. The article of claim 5, further comprising a nonwoven finger tab bonded to a terminal end region of the user-bond section.

7. The article of claim 5, wherein:

the garment comprises a liquid impermeable outer cover, a liquid permeable liner bonded to the outer cover, and an absorbent assembly disposed between the liner and outer cover;

the interior tape member is bonded to the liner; and the factory-bond section is bonded to the outer cover.

8. An article, comprising:

a garment having an inner surface intended to face the body during use, an opposite outer surface intended to face away from the body during use, a first end, a first waistband section contiguous with the first end, a second end, a second waistband section contiguous with the second end, an intermediate section which interconnects the waistband sections, and longitudinal sides extending between the first and second ends;

a substrative member containing printed information, the substrative member bonded to the inner surface of the first waistband section adjacent one of the longitudinal sides; and a tape fastener bonded to the first waistband section, the tape fastener comprising:

an interior tape member bonded to the inner surface to sandwich the substrative member between the interior tape member and the inner surface, the interior tape member formed of a transparent material and the printed information being visible through the interior tape member; and an exterior tape member having a factory-bond section bonded to the first waistband section and a user-bond section comprising an adhesive surface adapted to releasably engage the interior tape member, the user-bond section formed of a transparent material and the printed information being visible through the interior tape member and the user-bond section when the user-bond section is releasably engaged with the interior tape member.

9. The article of claim 8, wherein the exterior tape member and the interior tape member are bonded together.

10. The article of claim 8, further comprising a finger tab bonded to a terminal end region of the user-bond section.

* * * * *